(12) United States Patent
Areskoug et al.

(10) Patent No.: US 10,143,595 B2
(45) Date of Patent: Dec. 4, 2018

(54) PARTICLE-CONTAINING FOAM STRUCTURE

(75) Inventors: Stefan Areskoug, Molnycke (SE); Malin Prydz, Stora Hoga (SE); Magnus Nolmark, Gothenburg (SE)

(73) Assignee: MÖLNLYCKE HEALTH CARE AB, Göteborg (SE)

( * ) Notice: Subject to any disclaimer, the term of this patent is extended or adjusted under 35 U.S.C. 154(b) by 1460 days.

(21) Appl. No.: 12/528,364

(22) PCT Filed: Feb. 18, 2008

(86) PCT No.: PCT/EP2008/001237
§ 371 (c)(1),
(2), (4) Date: Aug. 24, 2009

(87) PCT Pub. No.: WO2008/101652
PCT Pub. Date: Aug. 28, 2008

(65) Prior Publication Data
US 2010/0286584 A1 Nov. 11, 2010

(30) Foreign Application Priority Data
Feb. 23, 2007 (EP) .................... 07003766

(51) Int. Cl.
*A61F 13/00* (2006.01)
*A61F 13/02* (2006.01)
(Continued)

(52) U.S. Cl.
CPC .......... *A61F 13/0213* (2013.01); *C08G 18/10* (2013.01); *C08G 18/4829* (2013.01);
(Continued)

(58) Field of Classification Search
CPC .. A61F 13/069; A61F 13/00063; A61F 13/02; A61F 13/00068; A61F 13/00042; A61F 13/0276
(Continued)

(56) References Cited

U.S. PATENT DOCUMENTS 4,843,105 A * 6/1989 Reischl et al. .................. 521/54
4,937,273 A 6/1990 Okuyama et al.
(Continued)

FOREIGN PATENT DOCUMENTS

CN 1478891 * 3/2004
CN 1478891 A * 3/2004
(Continued)

OTHER PUBLICATIONS

Marsh, Harry and Francisco Rodriguez-Reinoso; "Activated Carbon"; 1st Edition: Elsevier Ltd (2006). ISBN:978-0-08-044463-5; accessed from www.books.google.com (Jun. 14, 2014).*
(Continued)

*Primary Examiner* — Ophelia A Hawthorne
*Assistant Examiner* — Caitlin Carreiro
(74) *Attorney, Agent, or Firm* — Ballard Spahr LLP

(57) ABSTRACT

A method of producing a hydrophilic polyurethane foam structure containing inert activated carbon particles, includes the steps of: (a) providing a water phase containing a surfactant and dispersed inert particles; (b) providing a isocyanate-terminated polyether having functionality of more than 2; (c) mixing the water phase and the isocyanate-terminated polyether, immediately transferring the resulting mixture to a mold or a continuous web, whereby a foam structure is obtained; and (d) drying the foam structure until it has a moisture content of at most 10% (wt). A foam structure produced by the method and a wound dressing containing the foam structure are also disclosed.

10 Claims, 3 Drawing Sheets

(51) Int. Cl.
*C08G 18/10* (2006.01)
*C08G 18/48* (2006.01)
*A61F 13/06* (2006.01)
*C08G 101/00* (2006.01)

(52) U.S. Cl.
CPC ..... *A61F 13/069* (2013.01); *A61F 2013/0074* (2013.01); *C08G 2101/0083* (2013.01); *Y10T 428/249986* (2015.04)

(58) Field of Classification Search
USPC ............ 602/46; 206/440–441; 604/304–308; 424/445–449
See application file for complete search history.

(56) References Cited

U.S. PATENT DOCUMENTS

| | | | |
|---|---|---|---|
| 5,065,752 A * | 11/1991 | Sessions et al. | 602/46 |
| 5,858,911 A * | 1/1999 | Wellen et al. | 502/437 |
| 6,051,747 A | 4/2000 | Lindqvist et al. | |
| 6,207,875 B1 | 3/2001 | Lindqvist et al. | |
| 7,777,090 B2 * | 8/2010 | Park et al. | 602/42 |
| 2001/0003757 A1 | 6/2001 | Sakata et al. | |
| 2004/0127834 A1* | 7/2004 | Sigurjonsson et al. | 602/41 |
| 2010/0196501 A1 | 8/2010 | Areskoug et al. | |
| 2011/0028919 A1 | 2/2011 | Johnnison et al. | |

FOREIGN PATENT DOCUMENTS

| | | | | |
|---|---|---|---|---|
| CN | 1478891 A | 3/2004 | | |
| EP | 0 387 607 | 9/1990 | | |
| EP | 1 486 523 | 12/2004 | | |
| EP | 1486523 A1 * | 12/2004 | ............. | C08G 18/48 |
| GB | 1 507 232 | 4/1978 | | |
| WO | 97/42985 | 11/1997 | | |
| WO | WO 2004039421 A1 * | 5/2004 | | |

OTHER PUBLICATIONS

Marsh et al.; "Activated Carbon"; Elsevier (2006).*
International Search Report dated May 27, 2008, from corresponding PCT application.
Written Opinion dated May 27, 2008 for Intl. App. No. PCT/EP2008/001237, filed on Feb. 18, 2008 (Inventor—Areskoug et al.; Applicant—Molnlycke Health Care AB; pp. 1-7).
Preliminary Report on Patentability dated Jun. 22, 2009 for Intl. App. No. PCT/EP2008/001237, filed on Feb. 18, 2008 (Inventor—Areskoug et al.; Applicant—Molnlycke Health Care AB; pp. 1-9).
U.S. Pat. No. 6,051,747; Apr. 18, 2000.
PACER Listing of Docket Entries.
Stipulation of Dismissal; Sep. 16, 2008.
Deposition of Stephen J. Clarson, Ph.D.; Feb. 1, 2007.
Deposition of Stephen J. Clarson, Ph.D.; Mar. 6, 2008.
Markman Order; Jun. 21, 2007.
First Amended Complaint and Demand for Jury Trial; Jun. 15, 2006.
Preliminary Constructions of Defendants Medline Industries, Inc. and Ossur HF; Dec. 21, 2006.
Joint Claim Construction Statement; Jan. 16, 2007.
Exhibit A of Joint Claim Construction Statement—Parties' proposed constructions of each disputed claim term, phrase, or clause and support for such constructions; Jan. 16, 2007.
Exhibit B of Joint Claim Construction Statement—Summary of Opinions of Dr. Stephen J. Clarson; Jan. 16, 2007.
Claim Constructing Brief of Defendants Medline Industries, Inc. and Ossur HF; Feb. 7, 2007.
Molnlycke Health Care AB and Molnlycke Health Care US Opening Claim Construction Brief; Feb. 7, 2007.
Exhibit 1 of Molnlycke Health Care AB and Molnlycke Health Care US Opening Claim Construction Brief—U.S. Pat. No. 6,051,747; Feb. 7, 2007.
Exhibit 2, Parts A-I of Molnlycke Health Care AB and Molnlycke Health Care US Opening Claim Construction Brief—Gentleheal® Marketing Materials; Feb. 7, 2007.
Exhibit 3 of Molnlycke Health Care AB and Molnlycke Health Care US Opening Claim Construction Brief—Excerpts of Technical Dictionaries in the Chemical and Medical Fields; Feb. 7, 2007.
Exhibit 4 Parts A-E of Molnlycke Health Care AB and Molnlycke Health Care US Opening Claim Construction Brief—Excerpts of General purpose dictionaries; Feb. 7, 2007.
Exhibit 5 Parts A-B of Molnlycke Health Care AB and Molnlycke Health Care US Opening Claim Construction Brief—U.S. Pat. No. 7,154,017; Feb. 7, 2007.
Excerpts of Videotaped Deposition of Dr. Steven J. Clarson; Feb. 7, 2007.
Excerpts of Videotaped Deposition of Tomas T. Fabo; Feb. 7, 2007.
Responsive Claim Construction Brief of Defendants Medline Industries, Inc. and Ossur HF; Feb. 7, 2007.
Molnlycke Health Care AB and Molnlycke Health Care US Response to Medline Industries, Inc. and Ossur HF Opening Claim Construction Brief; Feb. 7, 2007.
Order; Jun. 21, 2007.
Molnlycke Health Care AB and Molnlycke Health Care US Consolidated Brief in Opposition to Defendants Medline Industries, Inc. and Ossur HF Cross-Motion to Amend and in Reply to Defendants Opposition to Motion for Protective Order; Nov. 5, 2007.
Exhibit A of Molnlycke Health Care AB and Molnlycke Health Care US Consolidated Brief in Opposition to Defendants Medline Industries, Inc. and Ossur HF Cross-Motion to Amend and in Reply to Defendants Opposition to Motion for Protective Order—U.S. Pat. No. 6,051,747; Nov. 5, 2007.
Exhibit B of Molnlycke Health Care AB and Molnlycke Health Care US Consolidated Brief in Opposition to Defendants Medline Industries, Inc. and Ossur HF Cross-Motion to Amend and in Reply to Defendants Opposition to Motion for Protective Order—Defendants Medline Industries, Inc. and Ossur HF Disclosure of Invalidity Contentions; Nov. 5, 2007.
Exhibit C of Molnlycke Health Care AB and Molnlycke Health Care US Consolidated Brief in Opposition to Defendants Medline Industries, Inc. and Ossur HF Cross-Motion to Amend and in Reply to Defendants Opposition to Motion for Protective Order—Excerpts of Jan. 31, 2007 Videotaped Deposition of Tomas T. Fabo; Nov. 5, 2007.
Exhibit D of Molnlycke Health Care AB and Molnlycke Health Care US Consolidated Brief in Opposition to Defendants Medline Industries, Inc. and Ossur HF Cross-Motion to Amend and in Reply to Defendants Opposition to Motion for Protective Order—Excerpts of Aug. 21, 2007 Videotaped Deposition of Tomas T. Fabo; Nov. 5, 2007.
Exhibit E of Molnlycke Health Care AB and Molnlycke Health Care US Consolidated Brief in Opposition to Defendants Medline Industries, Inc. and Ossur HF Cross-Motion to Amend and in Reply to Defendants Opposition to Motion for Protective Order—Correspondence dated Oct. 8, 2007 from Mr. Baldassare Vinti to Mr. Steve Moore; Nov. 5, 2007.
Exhibit F of Molnlycke Health Care AB and Molnlycke Health Care US Consolidated Brief in Opposition to Defendants Medline Industries, Inc. and Ossur HF Cross-Motion to Amend and in Reply to Defendants Opposition to Motion for Protective Order—Excerpts of Transcript of Jul. 25, 2007 Hearing; Nov. 5, 2007.
Exhibit G of Molnlycke Health Care AB and Molnlycke Health Care US Consolidated Brief in Opposition to Defendants Medline Industries, Inc. and Ossur HF Cross-Motion to Amend and in Reply to Defendants Opposition to Motion for Protective Order—Defendants' Objections and Responses to Plaintiffs' First Set of Continuing Interrogatories; Nov. 5, 2007.
Exhibit H of Molnlycke Health Care AB and Molnlycke Health Care US Consolidated Brief in Opposition to Defendants Medline Industries, Inc. and Ossur HF Cross-Motion to Amend and in Reply to Defendants Opposition to Motion for Protective Order—Excerpts of Transcript of Sep. 6, 2007 Deposition of Jonathan Primer; Nov. 5, 2007.
Exhibit I of Molnlycke Health Care AB and Molnlycke Health Care US Consolidated Brief in Opposition to Defendants Medline Indus-

(56) References Cited

OTHER PUBLICATIONS tries, Inc. and Ossur HF Cross-Motion to Amend and in Reply to Defendants Opposition to Motion for Protective Order—Excerpts of Transcript of Sep. 27, 2007 Deposition of Hilmar Jannusson; Nov. 5, 2007.
Exhibit J of Molnlycke Health Care AB and Molnlycke Health Care US Consolidated Brief in Opposition to Defendants Medline Industries, Inc. and Ossur HF Cross-Motion to Amend and in Reply to Defendants Opposition to Motion for Protective Order—Plaintiffs' Objections to Notice of 30(b)(6) Depositions Concerning the Issues of Infringement, Validity, and Enforceability; Nov. 5, 2007.
Medline Industries, Inc. and Ossur HF Motion for Summary Judgment of Invalidity; Mar. 26, 2008.
Medline Industries, Inc. and Ossur HF Memorandum of Law in Support of Motion for Summary Judgment of Invalidity; Mar. 26, 2008.
Medline Industries, Inc. and Ossur HF Rule 56.1 Statement of Undisputed Material Facts; Mar. 26, 2008.
Declaration of Jennifer R. Scullion in Support of Medline Industries, Inc. and Ossur HF Motion for Summary Judgment of Invalidity; Mar. 26, 2008.
Exhibit A of Medline Industries, Inc. and Ossur HF Rule 56.1 Statement of Undisputed Material Facts—U.S. Pat. No. 6,051,747; Mar. 26, 2008.
Exhibit B of Medline Industries, Inc. and Ossur HF Rule 56.1 Statement of Undisputed Material Facts—U.S. Pat. No. 4,921,704; Mar. 26, 2008.
Exhibit C of Medline Industries, Inc. and Ossur HF Rule 56.1 Statement of Undisputed Material Facts—U.S. Pat. No. 5,340,363; Mar. 26, 2008.
Exhibit D of Medline Industries, Inc. and Ossur HF Rule 56.1 Statement of Undisputed Material Facts—EP Patent No. 0 261 167; Mar. 26, 2008.
Exhibit E of Medline Industries, Inc. and Ossur HF Rule 56.1 Statement of Undisputed Material Facts—U.S. Pat. No. 5,540,922; Mar. 26, 2008.
Exhibit F of Medline Industries, Inc. and Ossur HF Rule 56.1 Statement of Undisputed Material Facts—U.S. Pat. No. 5,635,201; Mar. 26, 2008.
Exhibit G of Medline Industries, Inc. and Ossur HF Rule 56.1 Statement of Undisputed Material Facts—British Patent No. 898,826; Mar. 26, 2008.
Exhibit H of Medline Industries, Inc. and Ossur HF Rule 56.1 Statement of Undisputed Material Facts—Excerpts of Jan. 31, 2007 Videotaped Deposition of Tomas T. Fabo; Mar. 26, 2008.
Exhibit I of Medline Industries, Inc. and Ossur HF Rule 56.1 Statement of Undisputed Material Facts—Excerpts of Aug. 21, 2007 Videotaped Deposition of Tomas T. Fabo; Mar. 26, 2008.
Exhibit J of Medline Industries, Inc. and Ossur HF Rule 56.1 Statement of Undisputed Material Facts—Excerpts of Videotaped Deposition of Dr. Steven J. Clarson; Mar. 26, 2008.
Exhibit K of Medline Industries, Inc. and Ossur HF Rule 56.1 Statement of Undisputed Material Facts—Excerpts of Videotaped Deposition of Craig Broussard, Ph.D., R.N; Mar. 26, 2008.
Exhibit L of Medline Industries, Inc. and Ossur HF Rule 56.1 Statement of Undisputed Material Facts—Excerpts of Videotaped Deposition of Larry Bogart; v.
Exhibit M of Medline Industries, Inc. and Ossur HF Rule 56.1 Statement of Undisputed Material Facts—Excerpts of the Prosecution File of U.S. Pat. No. 6,051,747; Mar. 26, 2008.
Exhibit N of Medline Industries, Inc. and Ossur HF Rule 56.1 Statement of Undisputed Material Facts—Excerpts of the Prosecution File of U.S. Pat. No. 6,051,747; Mar. 26, 2008.
Exhibit O of Medline Industries, Inc. and Ossur HF Rule 56.1 Statement of Undisputed Material Facts—Excerpts of the Prosecution File of U.S. Pat. No. 6,051,747; Mar. 26, 2008.
Exhibit P of Medline Industries, Inc. and Ossur HF Rule 56.1 Statement of Undisputed Material Facts—Excerpts of the Prosecution File of U.S. Pat. No. 6,051,747; Mar. 26, 2008.
Exhibit Q of Medline Industries, Inc. and Ossur HF Rule 56.1 Statement of Undisputed Material Facts—Initial Memorandum of the Fabo Interference Proceeding; Mar. 26, 2008.
Exhibit R of Medline Industries, Inc. and Ossur HF Rule 56.1 Statement of Undisputed Material Facts—Sua Sponte Holding of Unpatentability in View of Prior Art; Mar. 26, 2008.
Exhibit S of Medline Industries, Inc. and Ossur HF Rule 56.1 Statement of Undisputed Material Facts—Molnlycke Health Care AB and Molnlycke Health Care US Supplemental Answers to Defendant Ossur HF's First Set of Interrogatories; Mar. 26, 2008.
Exhibit T of Medline Industries, Inc. and Ossur HF Rule 56.1 Statement of Undisputed Material Facts—Molnlycke Health Care AB and Molnlycke Health Care US Response to Medline Industries, Inc. and Ossur HF Claim Construction Brief; Mar. 26, 2008.
Expert Declaration of Dr. Michael A. Brook in Support of Medline Industries, Inc. and Ossur HF Motion for Summary Judgment; Mar. 26, 2008.
Exhibit A of Expert Declaration of Dr. Michael A. Brook in Support of Medline Industries, Inc. and Ossur HF Motion for Summary Judgment—Curriculum Vitae; Mar. 26, 2008.
Exhibit B of Expert Declaration of Dr. Michael A. Brook in Support of Medline Industries, Inc. and Ossur HF Motion for Summary Judgment—Expert Report of Michael A. Brook, Ph. D. on Validity Issues; Mar. 26, 2008.
Molnlycke Health Care AB and Molnlycke Health Care US Motion for Partial Summary Judgment That U.S. Pat. No. 6,051,747 is Not Invalid; Mar. 26, 2008.
Placeholder for Brief in Support of Molnlycke Health Care AB and Molnlycke Health Care US Motion for Partial Summary Judgment That U.S. Pat. No. 6,051,747 is Not Invalid Filed Under Seal Pursuant to Revised Protective Order Submitted to the Court on Sep. 21, 2007; Mar. 26, 2008.
Molnlycke Health Care AB and Molnlycke Health Care US Statement of Undisputed Material Facts in Support of Motion to Strike Medline Industries, Inc. and Ossur HF New and Untimely Noninfringing Alternative Theory, Including Exhibits 1-9 Filed Under Seal Pursuant to Revised Protective Order; Mar. 26, 2008.
U.S. Pat. No. 6,051,747; Mar. 26, 2008.
Excerpts of Videotaped Deposition of Andrew Martin Reed, Ph.D.; Mar. 26, 2008.
Excerpts of Videotaped Deposition of Laura Shafer; Mar. 26, 2008.
Excerpts of Videotaped Deposition of Craig Broussard, Ph.D., R.N; Mar. 26, 2008.
Excerpts of Videotaped Deposition of Larry Bogart; Mar. 26, 2008.
Placeholder for Exhibit 6—Molnlycke Health Care AB and Molnlycke Health Care US Motion for Partial Summary Judgment That U.S. Pat. No. 6,051,747 is Not Invalid; Confidential—Filed Under Seal Pursuant to Revised Protective Order Submitted to the Court on Sep. 21, 2007; Mar. 26, 2008.
Placeholder for Exhibit 7—Molnlycke Health Care AB and Molnlycke Health Care US Motion for Partial Summary Judgment That U.S. Pat. No. 6,051,747 is Not Invalid; Confidential—Filed Under Seal Pursuant to Revised Protective Order Submitted to the Court on Sep. 21, 2007; Mar. 26, 2008.
Placeholder for Exhibit 8—Molnlycke Health Care AB and Molnlycke Health Care US Motion for Partial Summary Judgment That U.S. Pat. No. 6,051,747 is Not Invalid; Confidential—Filed Under Seal Pursuant to Revised Protective Order Submitted to the Court on Sep. 21, 2007; Mar. 26, 2008.
Excerpts of Jan. 31, 2007 Videotaped Deposition of Tomas T. Fabo; Mar. 26, 2008.
Placeholder for Exhibit 10—Molnlycke Health Care AB and Molnlycke Health Care US Motion for Partial Summary Judgment That U.S. Pat. No. 6,051,747 is Not Invalid; Confidential—Filed Under Seal Pursuant to Revised Protective Order Submitted to the Court on Sep. 21, 2007; Mar. 26, 2008.
Placeholder for Exhibit 11—Molnlycke Health Care AB and Molnlycke Health Care US Motion for Partial Summary Judgment That U.S. Pat. No. 6,051,747 is Not Invalid; Confidential—Filed Under Seal Pursuant to Revised Protective Order Submitted to the Court on Sep. 21, 2007; Mar. 26, 2008.
Placeholder for Exhibit 12—Molnlycke Health Care AB and Molnlycke Health Care US Motion for Partial Summary Judgment That U.S.

(56) References Cited

OTHER PUBLICATIONS

Pat. No. 6,051,747 is Not Invalid; Confidential—Filed Under Seal Pursuant to Revised Protective Order Submitted to the Court on Sep. 21, 2007; Mar. 26, 2008.
Placeholder for Exhibit 13—Molnlycke Health Care AB and Molnlycke Health Care US Motion for Partial Summary Judgment That U.S. Pat. No. 6,051,747 is Not Invalid; Confidential—Filed Under Seal Pursuant to Revised Protective Order Submitted to the Court on Sep. 21, 2007; Mar. 26, 2008.
Placeholder for Exhibit 14—Molnlycke Health Care AB and Molnlycke Health Care US Motion for Partial Summary Judgment That U.S. Pat. No. 6,051,747 is Not Invalid; Confidential—Filed Under Seal Pursuant to Revised Protective Order Submitted to the Court on Sep. 21, 2007; Mar. 26, 2008.
Placeholder for Exhibit 15—Molnlycke Health Care AB and Molnlycke Health Care US Motion for Partial Summary Judgment That U.S. Pat. No. 6,051,747 is Not Invalid; Confidential—Filed Under Seal Pursuant to Revised Protective Order Submitted to the Court on Sep. 21, 2007; Mar. 26, 2008.
Placeholder for Exhibit 16—Molnlycke Health Care AB and Molnlycke Health Care US Motion for Partial Summary Judgment That U.S. Pat. No. 6,051,747 is Not Invalid; Confidential—Filed Under Seal Pursuant to Revised Protective Order Submitted to the Court on Sep. 21, 2007; Mar. 26, 2008.
Excerpts of Videotaped Deposition of James Wetrich; Mar. 26, 2008.
Placeholder for Exhibit 18—Molnlycke Health Care AB and Molnlycke Health Care US Motion for Partial Summary Judgment That U.S. Pat. No. 6,051,747 is Not Invalid; Confidential—Filed Under Seal Pursuant to Revised Protective Order Submitted to the Court on Sep. 21, 2007; Mar. 26, 2008.
Placeholder for Exhibit 19—Molnlycke Health Care AB and Molnlycke Health Care US Motion for Partial Summary Judgment That U.S. Pat. No. 6,051,747 is Not Invalid; Confidential—Filed Under Seal Pursuant to Revised Protective Order Submitted to the Court on Sep. 21, 2007; Mar. 26, 2008.
Placeholder for Exhibit 20—Molnlycke Health Care AB and Molnlycke Health Care US Motion for Partial Summary Judgment That U.S. Pat. No. 6,051,747 is Not Invalid; Confidential—Filed Under Seal Pursuant to Revised Protective Order Submitted to the Court on Sep. 21, 2007; Mar. 26, 2008.
U.S. Pat. No. 5,352,508; Mar. 26, 2008.
Excerpts of Deposition of Michael Brook; Mar. 26, 2008.
Molnlycke Health Care AB and Molnlycke Health Care US Brief in Opposition to Medline Industries, Inc. and Ossur HF Motion for Summary Judgment of Invalidity; Apr. 24, 2008.
Exhibit 23 of Molnlycke Health Care AB and Molnlycke Health Care US Brief in Opposition to Medline Industries, Inc. and Ossur HF Motion for Summary Judgment of Invalidity—Excerpts of videotaped deposition of Andrew Martin Reed, Ph. D.; Apr. 24, 2008.
Exhibit 24 of Molnlycke Health Care AB and Molnlycke Health Care US Brief in Opposition to Medline Industries, Inc. and Ossur HF Motion for Summary Judgment of Invalidity—Excerpts of Deposition of Michael Brook; Apr. 24, 2008.
Exhibit 25 of Molnlycke Health Care AB and Molnlycke Health Care US Brief in Opposition to Medline Industries, Inc. and Ossur HF Motion for Summary Judgment of Invalidity—Excerpts of Videotaped Deposition of Dr. Steven J. Clarson; Apr. 24, 2008.
Exhibit 26 of Molnlycke Health Care AB and Molnlycke Health Care US Brief in Opposition to Medline Industries, Inc. and Ossur HF Motion for Summary Judgment of Invalidity—Excerpts of Videotaped Deposition of Larry Bogart; Apr. 24, 2008.
Exhibit 27 of Molnlycke Health Care AB and Molnlycke Health Care US Brief in Opposition to Medline Industries, Inc. and Ossur HF Motion for Summary Judgment of Invalidity—Excerpts of Deposition of Benoit Castel; Apr. 24, 2008.
Exhibit 28 of Molnlycke Health Care AB and Molnlycke Health Care US Brief in Opposition to Medline Industries, Inc. and Ossur HF Motion for Summary Judgment of Invalidity—*Ortho-McNeil Pharm., Inc* v. *Mylan Labs., Inc.*, No. 2007-1223, 2008 WL 834402, at *5 (Fed. Cir. Mar. 31, 2008); Apr. 24, 2008.
Exhibit 29 of Molnlycke Health Care AB and Molnlycke Health Care US Brief in Opposition to Medline Industries, Inc. and Ossur HF Motion for Summary Judgment of Invalidity—Excerpts of Jan. 31, 2007 Videotaped Deposition of Tomas T. Fabo; Apr. 24, 2008.
Exhibit 30 of Molnlycke Health Care AB and Molnlycke Health Care US Brief in Opposition to Medline Industries, Inc. and Ossur HF Motion for Summary Judgment of Invalidity—Excerpts of Videotaped Deposition of Craig Broussard, Ph.D., R.N; Apr. 24, 2008.
Exhibit 31 of Molnlycke Health Care AB and Molnlycke Health Care US Brief in Opposition to Medline Industries, Inc. and Ossur HF Motion for Summary Judgment of Invalidity—Excerpts of the Prosecution File of U.S. Pat. No. 6,051,747; Apr. 24, 2008.
Declaration of Stephen J. Clarson, Ph.D.; Apr. 24, 2008.
Declaration of Tomas Fabo dated Apr. 24, 2008; Apr. 24, 2008.
Exhibit A of Declaration of Tomas Fabo—Sua Sponte Holding of Unpatentability in View of Prior Art; Apr. 24, 2008.
Exhibit B of Declaration of Tomas Fabo—Fabo Opposition to the Sua Sponte Holding of Unpatentability in View of Prior Art; Apr. 24, 2008.
Exhibit C of Declaration of Tomas Fabo—Declaration of Tomas Fabo dated Oct. 30, 1991; Apr. 24, 2008.
Exhibit D of Declaration of Tomas Fabo—Opinion on the Final Hearing before the Board of Patent Appeals and Interferences; Apr. 24, 2008.
Declaration of Larry Bogart; Apr. 24, 2008.
Exhibit A of Declaration of Larry Bogart—U.S. Pat. No. 5,856,245; Apr. 24, 2008.
Exhibit B of Declaration of Larry Bogart—U.S. Pat. No. 5,352,508; Apr. 24, 2008.
Medline Industries, Inc. and Ossur HF Memorandum of Law in Opposition to Molnlycke's Motion for Partial Summary Judgment; Apr. 24, 2008.
1. Medline Industries, Inc. and Ossur HF Response to Molnlycke Health Care AB and Molnlycke Health Care US Statement of Undisputed Material Facts, and 2. Medline Industries, Inc. and Ossur HF Counter-Statement of Additional Material Facts; Apr. 24, 2008.
Declaration of Jennifer R. Scullion in Support of Medline Industries, Inc. and Ossur HF Opposition to Molnlycke's Motion for Partial Summary Judgment; Apr. 24, 2008.
Exhibit U of Declaration of Jennifer R. Scullion in Support of Medline Industries, Inc. and Ossur HF Opposition to Molnlycke's Motion for Partial Summary Judgment—U.S. Pat. No. 5,409,472; Apr. 24, 2008.
Exhibit V of Declaration of Jennifer R. Scullion in Support of Medline Industries, Inc. and Ossur HF Opposition to Molnlycke's Motion for Partial Summary Judgment—U.S. Pat. No. 5,571,529; Apr. 24, 2008.
Exhibit W of Declaration of Jennifer R. Scullion in Support of Medline Industries, Inc. and Ossur HF Opposition to Molnlycke's Motion for Partial Summary Judgment—UK Patent Application GB 2 290 031; Apr. 24, 2008.
Exhibit X of Declaration of Jennifer R. Scullion in Support of Medline Industries, Inc. and Ossur HF Opposition to Molnlycke's Motion for Partial Summary Judgment—U.S. Pat. No. 3,972,328; Apr. 24, 2008.
Exhibit Y of Declaration of Jennifer R. Scullion in Support of Medline Industries, Inc. and Ossur HF Opposition to Molnlycke's Motion for Partial Summary Judgment—U.S. Pat. No. 5,209,965; Apr. 24, 2008.
Exhibit Z of Declaration of Jennifer R. Scullion in Support of Medline Industries, Inc. and Ossur HF Opposition to Molnlycke's Motion for Partial Summary Judgment—U.S. Pat. No. 5,445,604; Apr. 24, 2008.
Exhibit AA of Declaration of Jennifer R. Scullion in Support of Medline Industries, Inc. and Ossur HF Opposition to Molnlycke's Motion for Partial Summary Judgment—U.S. Pat. No. 5,098,500; Apr. 24, 2008.

(56) References Cited

OTHER PUBLICATIONS

Exhibit BB of Declaration of Jennifer R. Scullion in Support of Medline Industries and Ossur HF Opposition to Molnlycke's Motion for Partial Summary Judgment—U.S. Pat. No. 3,364,063; Apr. 24, 2008.
Exhibit CC of Declaration of Jennifer R. Scullion in Support of Medline Industries and Ossur HF Opposition to Molnlycke's Motion for Partial Summary Judgment—U.S. Pat. No. 5,782,787; Apr. 24, 2008.
Exhibit DD of Declaration of Jennifer R. Scullion in Support of Medline Industries and Ossur HF Opposition to Molnlycke's Motion for Partial Summary Judgment—U.S. Pat. No. 4,629,457; Apr. 24, 2008.
Exhibit EE of Declaration of Jennifer R. Scullion in Support of Medline Industries and Ossur HF Opposition to Molnlycke's Motion for Partial Summary Judgment—U.S. Pat. No. 3,645,835; Apr. 24, 2008.
Exhibit FF of Declaration of Jennifer R. Scullion in Support of Medline Industries and Ossur HF Opposition to Molnlycke's Motion for Partial Summary Judgment—U.S. Pat. No. 4,454,191; Apr. 24, 2008.
Exhibit GG of Declaration of Jennifer R. Scullion in Support of Medline Industries and Ossur HF Opposition to Molnlycke's Motion for Partial Summary Judgment—U.S. Pat. No. 4,773,409; Apr. 24, 2008.
Exhibit HH of Declaration of Jennifer R. Scullion in Support of Medline Industries and Ossur HF Opposition to Molnlycke's Motion for Partial Summary Judgment—Great Britain Patent No. 439,085; Apr. 24, 2008.
Exhibit II of Declaration of Jennifer R. Scullion in Support of Medline Industries and Ossur HF Opposition to Molnlycke's Motion for Partial Summary Judgment—European Patent No. 0 230 387; Apr. 24, 2008.
Exhibit JJ of Declaration of Jennifer R. Scullion in Support of Medline Industries and Ossur HF Opposition to Molnlycke's Motion for Partial Summary Judgment—U.S. Pat. No. 3,349,676; Apr. 24, 2008.
Exhibit KK of Declaration of Jennifer R. Scullion in Support of Medline Industries and Ossur HF Opposition to Molnlycke's Motion for Partial Summary Judgment—U.S. Pat. No. 4,838,253; Apr. 24, 2008.
Exhibit LL of Declaration of Jennifer R. Scullion in Support of Medline Industries and Ossur HF Opposition to Molnlycke's Motion for Partial Summary Judgment—US Patent Application 2004/0127839; Apr. 24, 2008.
Exhibit MM of Declaration of Jennifer R. Scullion in Support of Medline Industries and Ossur HF Opposition to Molnlycke's Motion for Partial Summary Judgment—Excerpts from the Jan. 31, 2007 Videotaped Deposition of Tomas Fabo; Apr. 24, 2008.
Exhibit NN of Declaration of Jennifer R. Scullion in Support of Medline Industries and Ossur HF Opposition to Molnlycke's Motion for Partial Summary Judgment—Excerpts from the Aug. 21, 2007 Video Deposition of Tomas Fabo; Apr. 24, 2008.
Exhibit OO of Declaration of Jennifer R. Scullion in Support of Medline Industries and Ossur HF Opposition to Molnlycke's Motion for Partial Summary Judgment—Excerpts from the Videotaped Deposition of Steven Clarson; Apr. 24, 2008.
Exhibit PP of Declaration of Jennifer R. Scullion in Support of Medline Industries and Ossur HF Opposition to Molnlycke's Motion for Partial Summary Judgment—Excerpts from the Videotaped Deposition of Craig Broussard; Apr. 24, 2008.
Exhibit QQ of Declaration of Jennifer R. Scullion in Support of Medline Industries and Ossur HF Opposition to Molnlycke's Motion for Partial Summary Judgment—Excerpts from the Videotaped Deposition of Larry Bogart; Apr. 24, 2008.
Exhibit RR of Declaration of Jennifer R. Scullion in Support of Medline Industries and Ossur HF Opposition to Molnlycke's Motion for Partial Summary Judgment—Excerpts from the Videotaped Deposition of Baldur Baldursson; Apr. 24, 2008.
Exhibit SS of Declaration of Jennifer R. Scullion in Support of Medline Industries and Ossur HF Opposition to Molnlycke's Motion for Partial Summary Judgment—Excerpts from the Videotaped Deposition of Laura Shafer; Apr. 24, 2008.
Exhibit TT of Declaration of Jennifer R. Scullion in Support of Medline Industries and Ossur HF Opposition to Molnlycke's Motion for Partial Summary Judgment—Excerpts from the Deposition of Hilmar Janusson; Apr. 24, 2008.
Exhibit VV of Declaration of Jennifer R. Scullion in Support of Medline Industries and Ossur HF Opposition to Molnlycke's Motion for Partial Summary Judgment—Excerpts from the Oct. 8, 2007 deposition of Bengt Lindquist; Apr. 24, 2008.
Exhibit WW of Declaration of Jennifer R. Scullion in Support of Medline Industries and Ossur HF Opposition to Molnlycke's Motion for Partial Summary Judgment—Excerpts from the Videotaped Deposition of Palmar Gudnason; Apr. 24, 2008.
Exhibit XX of Declaration of Jennifer R. Scullion in Support of Medline Industries and Ossur HF Opposition to Molnlycke's Motion for Partial Summary Judgment—Excerpts from the Feb. 28, 2008 Deposition of Michael Brook; Apr. 24, 2008.
Exhibit YY of Declaration of Jennifer R. Scullion in Support of Medline Industries, Inc. and Ossur HF Opposition to Molnlycke's Motion for Partial Summary Judgment—Excerpts from the Videotaped Deposition of Andrew Martin Reed, Ph. D.; Apr. 24, 2008.
Exhibit ZZ of Declaration of Jennifer R. Scullion in Support of Medline Industries, Inc. and Ossur HF Opposition to Molnlycke's Motion for Partial Summary Judgment—Excerpts from the Video Deposition of Staffan Kuuse; Apr. 24, 2008.
Exhibit CCC of Declaration of Jennifer R. Scullion in Support of Medline Industries and Ossur HF Opposition to Molnlycke's Motion for Partial Summary Judgment—Wound Care Project overview Exhibit No. 78; Apr. 24, 2008.
Exhibit DDD of Declaration of Jennifer R. Scullion in Support of Medline Industries and Ossur HF Opposition to Molnlycke's Motion for Partial Summary Judgment—Medline's Production No. MED 001810 through 001816; Exhibit No. 20; Apr. 24, 2008.
Exhibit LLL of Declaration of Jennifer R. Scullion in Support of Medline Industries and Ossur HF Opposition to Molnlycke's Motion for Partial Summary Judgment—Ossur's Production No. OS 046840 through 046851; Ulman et al., "Silicone Pressure Sensitive Adhesives for Healthcare Applications."; Apr. 24, 2008.
Exhibit MMM of Declaration of Jennifer R. Scullion in Support of Medline Industries and Ossur HF Opposition to Molnlycke's Motion for Partial Summary Judgment—Excerpt from the file for Patent Interference Proceeding No. 102,565; Apr. 24, 2008.
Exhibit NNN of Declaration of Jennifer R. Scullion in Support of Medline Industries and Ossur HF Opposition to Molnlycke's Motion for Partial Summary Judgment—Staffan Areskoug's Deposition Exhibit No. 6; "Design Input AiO-Dressing"; Apr. 24, 2008.
Expert Declaration of Dr. Michael A. Brook in Support of Medline Industries and Ossur HF Opposition to Molnlycke Health Care AB and Molnlycke Health Care US Motion for Partial Summary Judgment ; Apr. 24, 2008.
Exhibit C of Expert Declaration of Dr. Michael A. Brook in Support of Medline Industries and Ossur HF Opposition to Molnlycke Health Care AB and Molnlycke Health Care US Motion for Partial Summary Judgment—Expert Report of Michael A. Brook, Ph. D. on Validity Issues; Apr. 24, 2008.
Declaration of Andrew M. Reed, Ph.D. in Support of Medline Industries and Ossur HF Opposition to Molnlycke Health Care AB and Molnlycke Health Care US Motion for Partial Summary Judgment; Apr. 24, 2008.
Exhibit A of Declaration of Andrew M. Reed, Ph.D. In Support of Medline Industries and Ossur HF Opposition to Molnlycke Health Care AB and Molnlycke Health Care US Motion for Partial Summary Judgment—Curriculum Vitae of Andrew M. Reed; Apr. 24, 2008.
Exhibit B of Declaration of Andrew M. Reed, Ph.D. in Support of Medline Industries and Ossur HF Opposition to Molnlycke Health Care AB and Molnlycke Health Care US Motion for Partial Summary Judgment—Expert Report of Andrew M. Reed, Ph. D.; Apr. 24, 2008.

(56) References Cited

OTHER PUBLICATIONS

Molnlycke Health Care AB and Molnlycke Health Care US Reply Brief to Medline Industries and Ossur HF Opposition to Motion for Partial Summary Judgment that U.S. Pat. No. 6,051,747 is Not Invalid; May 23, 2008.
Excerpts of Feb. 1, 2007 Videotaped Deposition of Dr. Steven J. Clarson; May 23, 2008.
Excerpts of Videotaped Deposition of Stefan Areskoug; May 23, 2008.
Excerpts of Mar. 6, 2008 Videotaped Deposition of Dr. Steven J. Clarson (Taken by Medline Industries and Ossur HF); May 23, 2008.
Excerpts of Aug. 21, 2007 Video Deposition of: Mr Tomas Fabo; May 23, 2008.
Exhibit 36 of Molnlycke Health Care AB and Molnlycke Health Care US Reply Brief to Medline Industries and Ossur HF Opposition to Motion for Partial Summary Judgment that U.S. Pat. No. 6,051,747 Is Not Invalid; Filed Under Seal Pursuant to Protective Order; May 23, 2008.
Excerpts of Videotaped Deposition of James Wetrich; May 23, 2008.
Excerpts of Videotaped Deposition of Laura Shafer; May 23, 2008.
Excerpts of Videotaped Deposition of Craig Broussard, Ph.D., R.N.; May 23, 2008.
Excerpts of Videotaped Deposition of Larry Bogart; May 23, 2008.
Excerpts of Video Deposition of Staffan Kuuse; May 23, 2008.
Exhibit 42 of Molnlycke Health Care AB and Molnlycke Health Care US Reply Brief to Medline Industries and Ossur HF Opposition to Motion for Partial Summary Judgment that U.S. Pat. No. 6,051,747 Is Not Invalid; Filed Under Seal Pursuant to Protective Order; May 23, 2008.
Excerpts of Video Deposition of Elisabet Lundqvist; May 23, 2008.
Second Declaration of Larry Bogart; May 23, 2008.
Expert Report of Mr. Larry Bogart dated Dec. 28, 2007; May 23, 2008.
Medline Industries and Ossur HF Reply Memorandum in Support of Motion for Summary Judgment of Invalidity; May 23, 2008.
Appendix of Unreported Authorities; May 23, 2008.
Excerpts from Manual of Patent Examining Procedure (Jul. 1997 Revisions); May 23, 2008.
Transcript of Videotaped Deposition of Tomas T. Fabo on Jan. 31, 2007 (215 pages); Jan. 31, 2007.
Transcript of Videotaped Deposition of James Wetrich (199 pages); Jan. 31, 2007.

* cited by examiner

PARTICLE-CONTAINING FOAM STRUCTURE

The present invention relates to a hydrophilic polyurethane foam structure. More specifically, the hydrophilic foam structure contains an increased amount of inert small particles such as activated carbon both inside and on the outside of the cells of the foam. Furthermore, the invention provides a method for manufacturing said hydrophilic foam structure.

TECHNICAL BACKGROUND

WO 97/42985 discloses a wound dressing comprising a layer of absorbent foam material which includes a pattern of holes. The holes open out on that side of the foam material which lies proximal to the wearer's skin when the dressing is worn, and the layer of foam material is coated with a layer of skin-adhering hydrophobic gel, wherein those end parts of the walls of the holes in the foam material that lie proximal to the wearer's skin when the dressing is worn are gel-coated. Nothing is disclosed about adding compounds affecting absorption to the dressing.

EP-A1-1 486 523 and U.S. Pat. No. 4,937,273 both relate to polyurethane foams containing antimicrobial silver bound to zeolite particles. Nothing is disclosed about adding compounds affecting absorption to the dressing.

GB-A-1 507 232 discloses a polyurethane foam which is intended to resemble a natural sponge. The foam contains the pigment Calcotone Green. Nothing is disclosed about neither wound dressings nor activated carbon particles.

EP-A-1 486 523 relates to a polyurethane foam containing polymeric inorganic particles. The foam could be used in a mattress or sanitary mat. Nothing is disclosed about neither activated carbon particles nor wound dressings.

US 2001/0003757 A1 and EP-A1-0 387 607 describe polyurethane foams containing electroconductive carbon black. The foams are intended to be used as an electroconductive elastic member. Nothing is mentioned about neither activated carbon particles nor wound dressings.

U.S. Pat. No. 5,065,752 shows a polyurethane foam containing superabsorbent particles. The foam could be used in wound dressings. Nothing is disclosed about activated carbon particles.

There is a need for materials that can be used in wound dressings and that possess improved absorption characteristics compared to the existing materials used in wound dressings available on the market. Important absorption characteristics are the maximum or accumulated absorption capacity, i.e. the ability to absorb large volumes of wound exudate in case of heavily exuding wounds, and the retention capacity, i.e. the ability of the material to resist static pressure, such as may occur in relation to pressure ulcers and in treating e.g. venous leg ulcers when often a combination of absorbing dressings and compression bandages is applied.

SUMMARY OF THE INVENTION

The present invention provides a method of producing a hydrophilic polyurethane foam structure that can be used as a wound dressing. The method comprises the steps of (a) providing a water phase containing a surfactant; (b) providing a isocyanate-terminated polyether having functionality of more than 2; (c) mixing said water phase and said isocyanate-terminated polyether, immediately transferring the resulting mixture to a mould or a continuous web whereby a foam structure is obtained; and (d) drying said foam structure until it has a moisture content of at most 10% (wt);

The essential feature of the method is that the water phase in step a) also contains dispersed inert particles of activated carbon. Without wishing to be bound by a particular theory, it appears that activated carbon particles improve the maximum absorption and retention capacities of a hydrophilic polyurethane foam structure, which is beneficial from a wound-healing perspective.

Furthermore, it is preferred to line said mould or said continuous web with casting paper before the mixture is added in step c). Said casting paper is removed before the drying step d).

In the presence of a catalyst, it is also preferred to add one or more gel-forming silicone components, that by curing form a cross-linked silicone gel, to one surface of the foam structure obtained after step d). Said catalyst is preferably a platinum complex.

Finally, the present invention provides a hydrophilic polyurethane foam structure having a pore size between 30 and 1000 µm, wherein said structure can be obtained by the above disclosed method.

DETAILED DESCRIPTION OF THE INVENTION

Accordingly, the present invention provides a method for manufacturing a hydrophilic foam structure showing improved absorption characteristics.

The hydrophilic foam structure of the present invention is basically a hydrophilic polyurethane foam. Suitable hydrophilic polyurethane foams include those known as HYPOL foams. HYPOL foams can be made from HYPOL hydrophilic prepolymers marketed by Dow Chemicals.

The conformable hydrophilic polyurethane foam can be made by mixing together an isocyanate terminated polyether having functionality of more than two with a surfactant and water and casting the mixture onto a surface.

Preferred isocyanate terminated polyethers include HYPOL FHP 2000, 2001, 3000, 3001, 2002 and 2000HD marketed by Dow Chemicals. HYPOL polymers are described in a booklet published by W. R. Grace and Co. "Hypol: foamable hydrophilic polymers-laboratory procedures and foam formulations". Their preparation and use are disclosed in British Patent Specifications Nos. 1429711 and 1507232.

Suitable surfactants for forming conformable hydrophilic polymer foams include non-ionic surfactants. Favoured non-ionic surfactants are oxypropylene-oxyethylene block copolymers known as PLURONIC marketed by BASF Wyandotte. Preferred PLURONIC surfactants include L65, F87, P38, P75 and L62.

To prepare a typical foam, 100 parts by weight of HYPOL FHP 2000, 2001, 3000, 3001, 2002 or 2000HD is mixed with 0.3 to 7 parts by weight of surfactant or mixtures of surfactants, 0.5 to 2 parts by weight of inert particles such as active carbon, and 30 to 300 parts by weight of water and the foaming mixture cast onto a surface. Typical foaming mixtures have a cream time of about 20-30 s., a rise time of about 60-250 s, and a cure time of about 400-800 s. Moreover, suitable foam pore sizes may vary between 30 and 1000 µm.

As already mentioned the hydrophilic polyurethane foam structure of the present invention can on one side be coated with a silicone gel, by adding one or more gel-forming silicone components thereto and allow the added silicone to form a cross-linked gel by curing. The cross-linked silicone gel used as coating of the hydrophilic polyurethane foam structure of the present invention can conveniently be characterised in terms of its tensile strength, penetrability and peel strength. As the term is used herein, "tensile strength" means the maximum tensile load which can be applied (by means of a standard Instron tester) to a 5 cm wide, 3 mm thick strip of the cross-linked silicone gel in question.

The cross-linked silicone gel may be formed from various gel-forming silicone components and mixtures, such as e.g. from linear silicones having reactive groups thereon, as is known in the art. Preferably, the gels are formed by reaction between a vinyl-substituted silicone component and a hydride-containing silicone component in the presence of a suitable catalyst such as a platinum catalyst.

The gel-forming silicone components used may have a viscosity within the range of 100-10000 mPas, a number average molecular weight in the range 350 to 40,000, and may, for example, have from 0.004 to 0.4 mmoles reactive group/g.

When the silicone gels are formed by cross-linking a mixture of two or more silicone components, the molecular weights of the various components and/or their degree of substitution by reactive groups may be different. This allows gels having different physical properties to be formed merely by varying the proportions of the components.

The components for forming suitable cross-linked silicones for use in the hydrophilic polyurethane foam structure of the present invention are available from e.g. Wacker, under the reference WACKER SILIGEL 612.

As already mentioned, the structures of the present invention are formed by coating a sheet of foamed material with one or more non-crosslinked silicone components and then causing cross-linking to occur. In the case of gels formed by reacting vinyl groups of one component with hydride groups of the other component, such curing will generally be carried out in the presence of a catalyst such as a platinum complex at a concentration of from 5 to 15 ppm. In such a case, the gel may be formed by curing at room temperature over a period of several days, but elevated temperatures are preferably employed. For example, the silicone gels may be formed by curing at a temperature of from 40° to 120° C. and preferably at a temperature between 80° and 100° C. At a temperature of 80° C., curing will generally take from 10 seconds to 10 minutes, for example from 1 to 5 minutes. At a temperature of 50° C., curing will generally take from 10 minutes to 2 hours, for example from 15 minutes to 1 hour.

One example of chemically suitable gel (polydimethyl siloxane gel)-forming silicone components is a platinum-catalysed 2-component addition hardening RTV silicone, such as SILGEL 612 from Wacker-Chemie GmbH, Burghausen, Germany, and MED-6340 from NuSil Technology, Carpinteria, USA.

Accordingly, the present invention provides the above described hydrophilic foam structure as a dressing that is characterized by comprising an inert particle improving the absorption capacities of the foam and which is dispersed therein and a pattern of holes which open into that side of the foam material that lies proximal to the wearer's skin when in use. Preferably, the foam material has a coating of a layer of hydrophobic cross-linked silicone gel which adheres to the skin, and wherein the walls of the holes in the foam material are coated with gel at those end parts of said walls which lie proximal to the wearer's skin when the dressing is used.

In an embodiment intended e.g. for wounds from which fluid is exuded only slightly or in normal quantities, the foam structure has a pattern of holes comprised of the pores in the foam material. In case a cross-linked silicone gel is applied, said gel also extends slightly into the open pores of the foam material situated proximal to the gel layer, without closing said pores.

Preferably, the foam material is coated with a layer of liquid-impervious material on that side of the foam material that lies distal from the wearer's skin in use.

The dressing comprising foam structure with dispersed inert particles and having a silicone gel coating on the side intended towards the wearers skin, has a skin adhesion force F1 of 0.1-2.0 N, suitably 0.2-1.3 N and preferably 0.2-0.7 N.

In a first embodiment the silicone gel layer has a thickness of 0.05-1.0 mm.

In a second embodiment a pattern of holes is created in the foam material before placing said material on the mixture layer of gel-forming silicone components.

The invention will now be described in more detail with reference to the accompanying drawings, in which:

FIG. 1A is an enlarged view of one feature of the FIG. 1 illustration;

Figure 2:
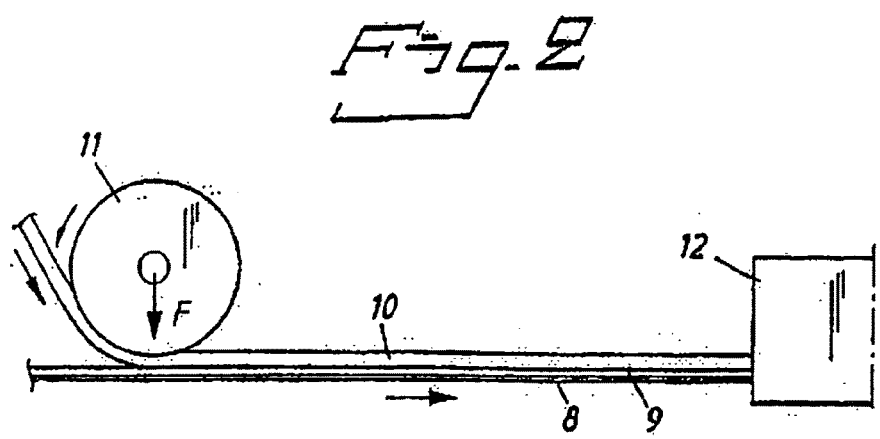
Figure 3:
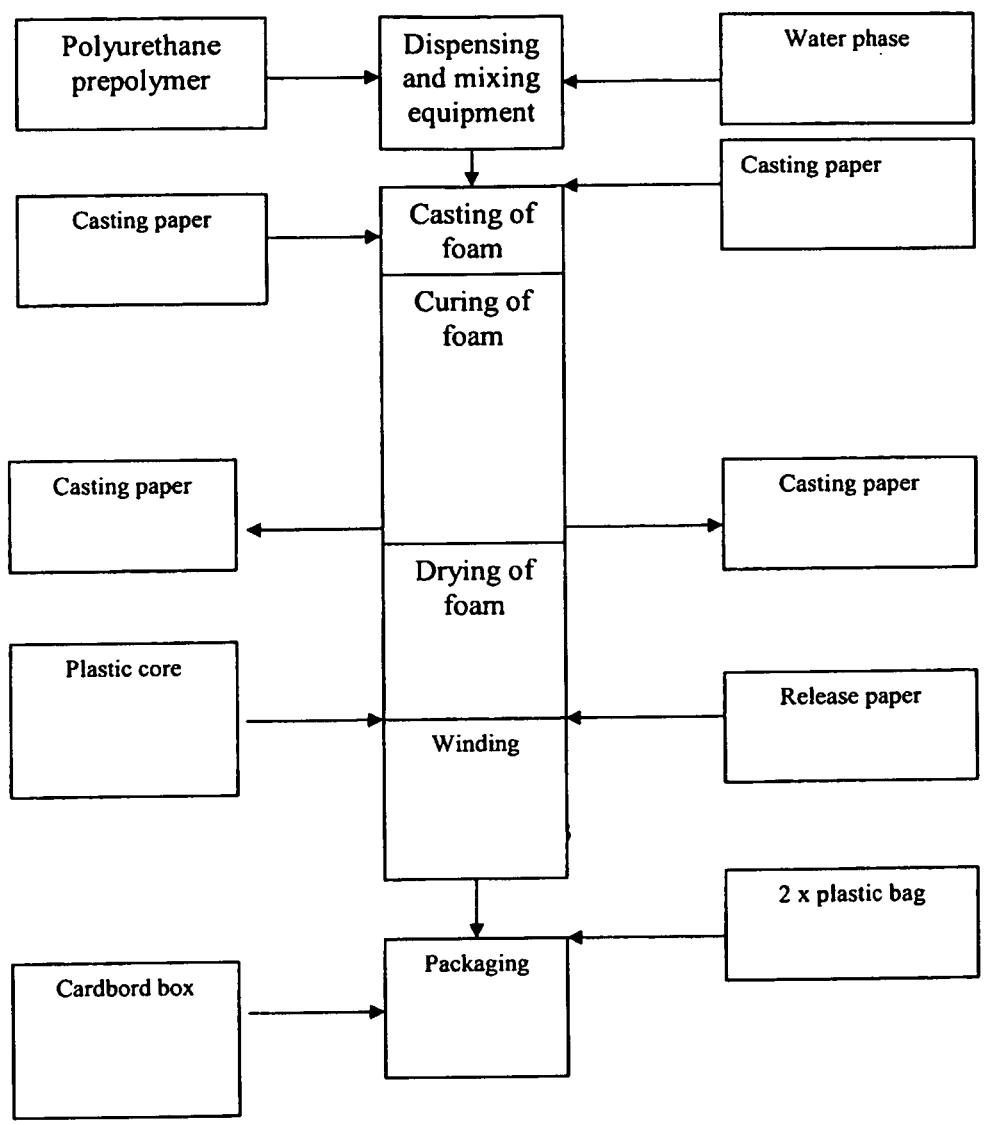

FIG. 2 schematically illustrates an apparatus for applying one or more gel-forming silicone components to a foam structure to obtain a silicone gel coating according to the present invention; and In one embodiment of the invention, the polyurethane pre-polymers are mixed with a water phase containing surfactants and inert particles such as activated carbon in dispensing and mixing equipment. The reaction mixture is subsequently transferred to a mould or a continuous web that has been lined with casting paper. After the termination of the polymerisation reaction, the casting paper is removed from the castings and the obtained foam is dried to a moisture content of at most 10% (wt). A plastic liquid-impervious core is coated.

Figure 1:
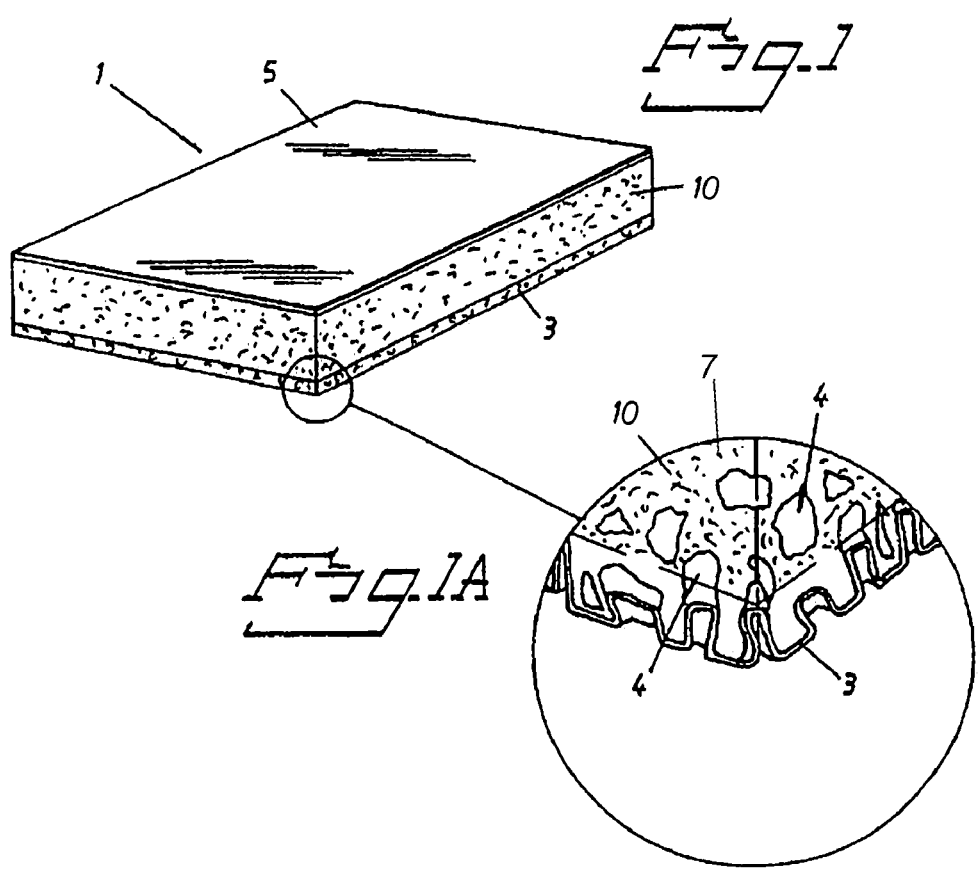
FIG. 1 is a schematic perspective view of a piece of an inventive dressing 1 according to one embodiment.

FIG. 1 illustrates a piece of a dressing 1 according to one embodiment of the invention. The dressing is comprised of an absorbent foam material 10 comprising activated carbon particles 7, which is coated with a gel layer 3 on that side which lies proximal to the wound or skin of the wearer when the dressing is used. As illustrated schematically in Figure IA, the gel layer 3 is disposed so that even a part of the walls of the open cells or pores 4 in the foam material that open into the gel-coated side thereof are gel coated. Because the gel layer 3 does not close, but only covers, a part of the walls in an end portion of the pores of the foam material that face the wound, excess wound fluid can be drawn into the foam material 10 and absorbed thereby. The gel layer also prevents the foam material from coming into direct contact with the wound or skin of the wearer. The thickness of the total gel layer, i.e. including the depth of penetration into the pores of the foam material, is 0.1-2.0 mm. Some of the pores in the foam material that face towards the wound are closed by the gel layer.

With the intention of providing a dressing that has a dry outer surface, the dressing is given a liquid-impervious layer 5 on the side opposite to the gel layer 3. This liquid-impervious layer 5 may conveniently comprise a thin liquid-impervious, but vapour-permeable, plastic film, for instance a polyurethane film.

The dressing illustrated in FIG. 1 is intended to be used with wounds that exude fluid in quantities ranging from slight to normal. The foam layer has a thickness of 1-10 mm, preferably 2-6 mm. As mentioned before, the foam material functions both as an absorbent and as a gel carrier, and the dressing as a whole will therefore be very soft and pliant. Because the gel adheres to the skin surrounding the wound, the dressing will be held in place while the gel affords a sealing function and prevents maceration, i.e. prevents wound fluid from running over healthy skin and softening and eventually damaging the epidermis. The open structure of the gel layer and the foam material also enables the skin to breathe. The nature of the adhesive gel used in this invention differs totally from the nature of glues that are typically used to secure dressings, for instance the acrylate glues or the hot melt glues that are used today to this end. The significant difference between these glues and the gel used in accordance with the invention is that the gel is much softer and has a better "wetting ability" than said glues.

This enables the gels to be given a much lower specific adhesiveness, i.e. lower adhesion per unit of contact surface area, than the specific adhesiveness that must be given to harder glues in order to achieve an equally effective total adhesion as that offered by the gel.

FIG. 2 is a highly schematic illustration of an apparatus for use in applying a layer of one or more gel-forming silicone components to a structure according to the present invention. The illustrated apparatus includes a conveyer (not shown) on which a plastic film 8 is conveyed from left to right in FIG. 2. A layer of uncured gel mixture 9 is placed on the film 8. By gel mixture is meant a mixture of those components which form a gel after curing, including polymers that can react with one another to form a cross-linked structure. A layer of absorbent foam material 10 is applied to the layer of uncured gel mixture 9 with the aid of a roller 11, and the layers 9, 10 are then transported into an oven 12. The gel mixture is cured in its passage through the oven 12 and forms a gel layer on the underside of the foam material.

It has been found that with suitable selection of the one or more gel-forming components and mixtures and proportions thereof, pressure force F, quantity of gel mixture, time between applying foam material and heating the layers, curing temperature, and so on, there will be formed a discontinuous gel coating on the foam material. This is because the gel mixture is drawn by capillary action into those pores or holes in the foam material that open out in that side of the foam material which lies in abutment with the gel mixture. When applying a gel-forming coating to foam material that lacks holes other than pores, the gel mixture must be applied in a layer of such thinness as to ensure that an excessively large number of the pores opening into the underside of the foam material will not be clogged or blocked by the gel coating. The viscosity of the gel mixture and the size of the pores in the foam material also influence the tendency of the mixture to penetrate into the pores. It has been found that the gel mixture layer should preferably be applied at a thickness of 0.05-1.00 mm. A larger part of the gel mixture layer is sucked into the foam, wherewith the total gel layer, including air and foam, will have a thickness of 0.10-2.00 mm.

In a first application of the above method for coating the underside of an polyurethane foam sheet with silicone gel, there was used an open cell, soft hydrophilic polyurethane foam sheet having a density of 130 kg/m and a thickness of 5 mm.

The silicone mixture was prepared from SILGEL 612 obtained from Wacker, in an A-component and B-component mixing ratio of 1.0:0.9. The uncured mixture had a viscosity of about 1000 mPa.

The polyurethane foam material was placed on a silicone gel mixture having a thickness of 0.2 mm, without applying pressure F from the roller 11, in other words the silicone mixture was subjected solely to the weight of the foam sheet. The time taken to transport the foam material 10 and the underlying silicone mixture 9 from the roller 11 to the oven 12 was one minute and the curing temperature was 130° C. The silicone cured in an oven within minutes. A polyurethane film of high vapour permeability and a thickness of 0.025 mm was then firmly glued to the foam on the side thereof opposite to the gel coating. At this mixture ratio, the silicone gel had a penetration death of 16 mm, and the skin adhesion force of the dressing was measured as 0.42 N. Under these conditions, it has been found that the gel mixture layer will preferably have a thickness of at least 0.1 mm, so as to obtain a suitable discontinuous gel coating on the foam material.

When the thickness of the gel mixture layer was greater than 0.4 mm, an excessively large percentage of the pores in the foam material became blocked, resulting in insufficient permeability of the gel coating.

It will be evident from the aforegoing that when carrying out the method described with reference to FIG. 2, the quality of the end product will depend on many factors. It is therefore not possible to provide these factors with general limit values, and such limit values must be established empirically with respect to the gel mixture and the foam material used.

The described method thus enables a dressing of the kind described with reference to FIG. 1 to be produced very easily. The method is also very flexible and enables dressings of mutually different absorbencies to be produced in principle by the same way and with the aid of the same apparatus.

The described dressing can, of course, be sterilized, e.g. by ethylene oxide sterilization or steam sterilization, and is intended for delivery in different sizes and for different types of wounds, both sterile packed and non-sterile packed. Because of their softness, they are suitable for use in combination with compression bandages and can be used beneficially on blisters, leg ulcers and like wounds. Their high degree of flexibility also makes them suitable for use on joint sores, such as knee sores and elbow sores, even in later phases of the sore healing process. The dressings can also be cut to a size suitable for the size of the sore or wound in question.

It will be understood that the above described exemplifying embodiments can be modified within the scope of the invention, particularly with respect to the described materials and process parameters applied.

The invention will now be further described in the enclosed examples.

Example 1: Manufacturing a Hydrophilic Polyurethane Foam Structure

A water phase for the foam-manufacturing process was prepared by dissolving/dispersing the non-ionic surfactant PLURONIC F87, and activated carbon. The final concentrations of these constituents in the water phase amounted to 0.1% (wt) of PLURONIC F87, and 1.0% (wt) of active carbon.

Simultaneously, a mould lined with casting paper was prepared. The mould had a sufficient depth so that sheet-formed foam castings having a thickness of 5 mm could be produced. The pre-polymer HYPOL 2001 (a isocyanate-terminated polyether) was added to the water phase in a dispensing and mixing equipment in an amount of 40% (wt) at room temperature. The resulting mixture was immediately transferred to the casting mould. The foaming amounted to 30 s, and then the foam was cured for 10 minutes. After curing, the casting papers were removed and the foam was dried to a moisture content of at most 10% (wt) at a temperature of 120° C.

Example 2: Water Absorption of the Hydrophilic Polyurethane Foam Structure

Seven batches of hydrophilic polyurethane foam structures were prepared in accordance with the process of Example 1. Four of the batches contained 1% (wt) of particles of activated carbon. Samples from each batch were soaked in tap water and allowed to absorb for 2 minutes. Subsequently, the samples were hung in one corner to drip off for 9 minutes. The length was measured in the cross direction (CD) and the width in the machine direction (MD). The length and width in the wet state were measured after the samples had dripped off. At least three samples have punched out of each batch.

The results obtained can be found in Table 1:

TABLE 1

| Batch | Activ. carbon? | Original thickness (mm) | Density (kg/m$^3$) | Absorption capacity (g/g) | Swelling length (%) | Swelling width (%) | Swelling thickness (%) | Number Of samples |
|---|---|---|---|---|---|---|---|---|
| 1 | No | 5.58 | 90.1 | 9.86 | 21.7 | 21.3 | 32.0 | 3 |
| 2 | No | 5.38 | 88.6 | 9.80 | 22.5 | 21.3 | 33.2 | 3 |
| 3 | No | 5.48 | 86.0 | 10.62 | 20.8 | 21.8 | 31.2 | 4 |
| 4 | Yes | 5.25 | 89.6 | 12.60 | 23.0 | 21.3 | 28.5 | 3 |
| 5 | Yes | 5.87 | 86.0 | 13.85 | 23.0 | 19.8 | n.d. | 4 |
| 6 | Yes | 5.11 | 91.7 | 13.60 | 21.9 | 21.2 | 26.8 | 3 |
| 7 | Yes | 5.27 | 92.4 | 12.48 | 22.9 | 20.8 | 26.8 | 4 | n.d. = not detected

The results show that the absorption capacity is about 30% higher for batches containing inert particles compared to batches without particles.

Example 3: Retention of a Saline Under Pressure

Seven batches of hydrophilic polyurethane foam structures were prepared in accordance with the process of Example 1. Four of the batches contained 1% (wt) of particles of activated carbon. Samples from all batches were punched as 10×10 cm pieces with rounded corners. First of all, the maximum absorption capacity was determined. The samples were weighed, subsequently soaked in a 0.9% (wt) aqueous solution of NaCl for five minutes and then drained for two minutes by hanging in a clip fastened in a corner. Finally, the samples were reweighed and the maximum absorption capacity was determined.

Dry samples were weighed, and then exposed to an amount of saline corresponding to 80% of the maximum absorption capacity of the samples. The areas of the samples were determined after the samples had been exposed to the saline. Subsequently, the samples were exposed to a static pressure of 40 mmHg for 5 minutes and finally reweighed. The retention of saline is calculated as the difference between the mass after the pressure treatment and the mass of the dry sample.

The results obtained can be found in Table 2, below:

| | Batch | | | | | | |
|---|---|---|---|---|---|---|---|
| | 1 | 2 | 3 | 4 | 5 | 6 | 7 |
| Active carbon? | No | No | No | Yes | Yes | Yes | Yes |
| Added liquid % of max. absorption | 80 | 80 | 80 | 87 | 80 | 80 | 80 |
| Area of sample (m$^2$) | 0.0132 | 0.0132 | 0.0132 | 0.0132 | 0.0132 | 0.0132 | 0.0132 |
| Dry weight of sample (g) | 6.57 | 6.69 | 6.66 | 6.65 | 6.66 | 6.68 | 6.92 |
| Retention after static pressure (g) | 7.27 | 9.13 | 9.61 | 18.51 | 16.12 | 17.93 | 10.86 |
| Retention after static pressure (% of max. absorption) | 18 | 23 | 23 | 34 | 32 | 33 | 25 |
| Amount of samples | 5 | 5 | 5 | 5 | 5 | 5 | 5 |

The obtained results show that the retention after static pressure is significantly higher for foam structures containing inert particles.

The invention claimed is:

1. A hydrophilic polyurethane foam structure having a pore size between 30 and 1000 µm, wherein the structure contains dispersed inert activated carbon particles, and wherein the structure is obtained by a method comprising the steps of
   a) providing a water phase containing a surfactant;
   b) providing an isocyanate-terminated polyether having functionality of more than 2;
   c) mixing the water phase and the isocyanate-terminated polyether, immediately transferring the resulting mixture to a mould or a continuous web, whereby a foam structure is obtained; and
   d) drying the foam structure until it has a moisture content of at most 10% (wt);
   wherein the water phase in step a) also contains dispersed inert activated carbon particles,
   wherein the inert activated carbon particles improve the maximum water absorption of the foam structure.

2. A wound dressing comprising the foam structure of claim 1.

3. An article comprising a wound dressing comprising a hydrophilic polyurethane foam structure having a pore size between 30 and 1000 µm, wherein the structure contains dispersed inert activated carbon particles, wherein the inert activated carbon particles improve the maximum water absorption of the foam structure.

4. The article of claim 3, wherein the inert activated carbon particles improve the water retention capacity of the foam structure.

5. The foam structure of claim 1, wherein the inert activated carbon particles improve the water retention capacity of the foam structure.

6. The wound dressing of claim 2, wherein the inert activated carbon particles improve the water retention capacity of the foam structure.

7. The article of claim 3, wherein the wound dressing further comprises a cross-linked silicone gel.

8. A method of preventing wound fluid from running over skin surrounding a wound, comprising applying the article of claim 7 over a wound and to skin surrounding the wound, wherein the cross-linked silicone gel adheres to the skin surrounding the wound, thereby preventing wound fluid from running over the skin surrounding the wound.

9. A method of using the article of claim 3, comprising applying the article of claim 3 over a wound and to skin surrounding the wound.

10. The article of claim 3, wherein the gram per gram water absorption capacity of the hydrophilic polyurethane foam structure is from 18% to 41% higher than a hydrophilic polyurethane foam structure without the dispersed inert activated carbon particles when the hydrophilic polyurethane foam structure comprises 1% wt of inert activated carbon particles.

\* \* \* \* \*